United States Patent [19]

Hidaka et al.

[11] Patent Number: 4,510,307

[45] Date of Patent: Apr. 9, 1985

[54] 6-QUINAZOLINESULFONYL DERIVATIVES AND PROCESS FOR PREPARATION THEREOF

[75] Inventors: Hiroyoshi Hidaka, Tsu; Takanori Sone, Nobeoka; Yasuharu Sasaki, Nobeoka; Taisuke Sugihara, Nobeoka; Seiji Takagi, Nobeoka; Kiyohide Sako, Nobeoka, all of Japan

[73] Assignee: Asahi Kasei Kogyo Kabushiki Kaisha, Japan

[21] Appl. No.: 293,192

[22] Filed: Aug. 17, 1981

[30] Foreign Application Priority Data

Aug. 20, 1980 [JP] Japan ................................ 55-113401
Aug. 22, 1980 [JP] Japan ................................ 55-114658
Jan. 29, 1981 [JP] Japan ................................ 56-10847

[51] Int. Cl.³ .............. C07D 265/00; C07D 247/00; C07D 403/00
[52] U.S. Cl. .................... 544/283; 544/122; 544/284; 544/287; 544/288; 544/293; 514/929
[58] Field of Search ............. 544/122, 283, 284, 287, 544/288, 293; 542/431

[56] References Cited

U.S. PATENT DOCUMENTS 3,595,861  7/1971  Bell et al. ............................ 544/283
3,702,849  11/1972 Cronin et al. ........................ 544/287
3,769,286  10/1973 Hess ..................................... 544/283
3,812,127  5/1974  Cronin et al. ........................ 544/283

Primary Examiner—Arthur P. Demers
Attorney, Agent, or Firm—Finnegan, Henderson, Farabow, Garrett & Dunner

[57] ABSTRACT

A 6-quinazolinesulfonyl derivative of Formula (I):

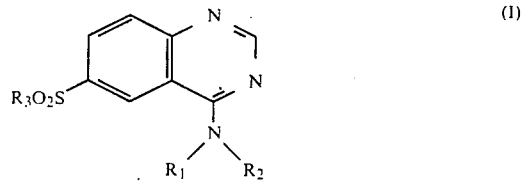

wherein
$R_1$ is a hydrogen atom or a $C_{1-12}$ alkyl group:
$R_2$ is a hydrogen atom, a $C_{1-12}$ alkyl group, a $C_{4-10}$ cycloalkyl group, an aryl group or an aralkyl group; and
$R_1$ and $R_2$ may be linked directly or through an oxygen atom to form a 5- to 7-membered heterocyclic ring together with the adjacent nitrogen atom; and
$R_3$ is a

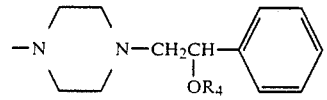

group wherein $R_4$ is a $C_{1-8}$ alkyl group; a —HN(CH$_2$)$_n$NH$_2$ group wherein n is an integer of 2 to 10; or a

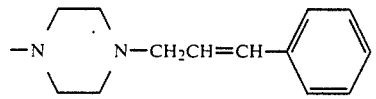

group;
and the pharmaceutically acceptable salt thereof; and a process for the preparation thereof. The compounds of this invention have a relaxatory action for vascular smooth muscle and are useful as a vasodilator and a hypotensor.

74 Claims, No Drawings

6-QUINAZOLINESULFONYL DERIVATIVES AND PROCESS FOR PREPARATION THEREOF

BACKGROUND OF THE INVENTION

1. Field of the Invention

This invention relates to novel 6-quinazolinesulfonyl derivatives which possess a relaxatory action for vascular smooth muscle and are useful as a vasodilator and a hypotensor, and a process for the preparation thereof.

2. Summary of the Invention

According to the present invention in one embodiment there is provided a 6-quinazolinesulfonyl derivative of Formula (I):

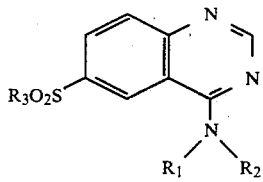

wherein $R_1$ is a hydrogen atom or a $C_{1-12}$ alkyl group;

$R_2$ is a hydrogen atom, a $C_{1-12}$ alkyl group, a $C_{4-10}$ cycloalkyl group, an aryl group or an aralkyl group; and $R_1$ and $R_2$ may be linked directly or through an oxygen atom to form a 5- to 7-membered heterocyclic ring together with the adjacent nitrogen atom; and $R_3$ is a

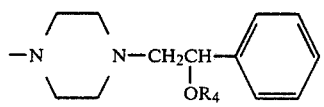

group wherein $R_4$ is a $C_{1-8}$ alkyl group; a $-NH(CH_2)_nNH_2$ group wherein n is an integer of 2 to 10; or a

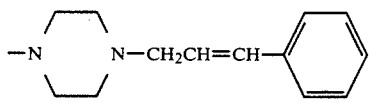

group;

and the pharmaceutically acceptable acid addition salt thereof.

The present invention in another embodiment provides a process of preparing the above described 6-quinazolinesulfonyl derivative.

DETAILED DESCRIPTION OF THE INVENTION

Exemplary $R_1$ groups in Formula (I) include a hydrogen atom; and $C_{1-12}$ alkyl groups, preferably $C_{1-6}$ alkyl groups, such as methyl, ethyl, n-propyl, isopropyl, n-butyl, isobutyl, sec-butyl, tert-butyl, n-pentyl, isopentyl, n-hexyl, n-heptyl, n-octyl, n-nonyl and n-dodecyl. Exemplary $R_2$ groups include a hydrogen atom; $C_{1-12}$ alkyl groups, preferably $C_{1-6}$ alkyl groups, such as methyl, ethyl, n-propyl, isopropyl, n-butyl, isobutyl, sec-butyl, tert-butyl, n-pentyl, isopentyl, n-hexyl, n-heptyl, n-octyl, n-nonyl and n-dodecyl; $C_{4-10}$ cycloalkyl groups, preferably $C_{5-7}$ cycloalkyl groups, such as cyclobutyl, cyclopentyl, cyclohexyl and cycloheptyl and cyclooctyl; aryl groups such as phenyl, naphthyl, o-, m- or p-chlorophenyl, p-bromophenyl, p-fluorophenyl, o-, m- or p-tolyl and 2,3-dimethylphenyl; and aralkyl groups such as benzyl, α-phenethyl, β-phenethyl, o-, m- or p-chlorobenzyl and p-fluorobenzyl. Exemplary 5- to 7-membered heterocyclic rings formed by linking $R_1$ and $R_2$ directly or through an oxygen atom together with the adjacent nitrogen atom include 1-pyrrolidinyl, piperidino, homopiperidino and morpholino groups.

Preferred

groups include amino, dimethylamino, diethylamino, di-n-propylamino, diisopropylamino, di-n-butylamino, diisobutylamino, di-n-hexylamino, cyclopenthylamino, cyclohexylamino, cycloheptylamino, anilino, benzylamino, phenethylamino, N-methyl-N-cyclopentylamino, N-methyl-N-cyclohexylamino, N-n-propyl-N-cyclohexylamino, N-n-butyl-N-cyclohexylamino, N-isobutyl-N-cyclohexylamino, N-methylanilino, N-ethylanilino, N-butylanilino, N-methyl-N-benzylamino, N-methyl-N-phenethylamino, 1-pyrrolidinyl, piperidino, homopiperidino and morpholino groups.

Exemplary $R_3$ groups include

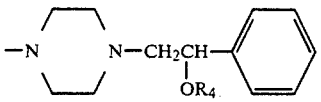

groups wherein $R_4$ is a $C_{1-8}$ alkyl group, preferably a $C_{1-4}$ alkyl group such as methyl, ethyl, n-propyl, isopropyl, n-butyl, isobutyl, n-pentyl, n-hexyl, n-heptyl and n-octyl groups; $-HN(CH_2)_nNH_2$ groups such as 2-aminoethylamino, 3-aminopropylamino, 4-aminobutylamino, 5-aminopentylamino, 6-aminohexylamino, 8-aminooctylamino and 10-aminodecylamino groups; and

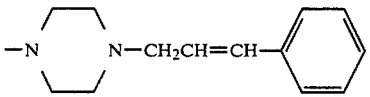

group.

Exemplary 6-quinazolinesulfonyl derivatives of this invention include:

1-(4-amino-6-quinazolinesulfonyl)-4-(2-ethoxy-2-phenylethyl)piperazine [referred to as "Compound (1)"];

1-(4-dimethylamino-6-quinazolinesulfonyl)-4-(2-ethoxy-2-phenylethyl)-piperazine [referred to as "Compound (2)"];

1-(4-diethylamino-6-quinazolinesulfonyl)-4-(2-ethoxy-2-phenylethyl)-piperazine [referred to as "Compound (3)"];

1-(4-dibutylamino-6-quinazolinesulfonyl)-4-(2-ethoxy-2-phenylethyl)-piperazine [referred to as "Compound (4)"];

1-(4-piperidino-6-quinazolinesulfonyl)-4-(2-methoxy-2-phenylethyl)-piperazine [referred to as "Compound (5)"];

1-(4-piperidino-6-quinazolinesulfonyl)-4-(2-ethoxy-2-phenylethyl)-piperazine [referred to as "Compound (6)"];

1-(4-piperidino-6-quinazolinesulfonyl)-4-(2-isopropoxy-2-phenylethyl)-piperazine [referred to as "Compound (7)"];

1-(4-piperidino-6-quinazolinesulfonyl)-4-(2-isobutoxy-2-phenylethyl)-piperazine [referred to as "Compound (8)"];

1-(4-piperidino-6-quinazolinesulfonyl)-4-cinnamylpiperazine [referred to as "Compound (9)"];

1-(4-dimethylamino-6-quinazolinesulfonyl)-4-cinnamylpiperazine [referred to as "Compound (10)"];

1-(4-diethylamino-6-quinazolinesulfonyl)-4-cinnamylpiperazine [referred to as "Compound (11)"];

1-(4-dibutylamino-6-quinazolinesulfonyl)-4-cinnamylpiperazine [referred to as "Compound (12)"];

1-[4-(1-pyrrolidinyl)-6-quinazolinesulfonyl]-4-(2-ethoxy-2-phenylethyl)-piperazine [referred to as "Compound (13)"];

1-(4-morpholino-6-quinazolinesulfonyl)-4-(2-ethoxy-2-phenylethyl)-piperazine [referred to as "Compound (14)"];

1-(4-cyclohexylamino-6-quinazolinesulfonyl)-4-(2-ethoxy-2-phenylethyl)-piperazine [referred to as "Compound (15)"];

1-(4-anilino-6-quinazolinesulfonyl)-4-(2-ethoxy-2-phenylethyl)piperazine [referred to as "Compound (16)"];

1-(4-benzylamino-6-quinazolinesulfonyl)-4-(2-ethoxy-2-phenylethyl)-4-(2-ethoxy-2-phenylethyl)piperazine [referred to as "Compound (17)"];

1-[4-(N-methyl-N-cyclopentylamino)-6-quinazolinesulfonyl]-4-(2-ethoxy-2-phenylethyl)piperazine [referred to as "Compound (18)"];

1-[4-(N-methyl-N-cyclohexylamino)-6-quinazolinesulfonyl]-4-(2-ethoxy-2-phenylethyl)piperazine [referred to as "Compound (19)"];

1-[4-(N-methyl-N-cycloheptylamino)-6-quinazolinesulfonyl]-4-(2-ethoxy-2-phenylethyl)piperazine [referred to as "Compound (20)"];

1-[4-(N-ethyl-N-cyclohexylamino)-6-quinazolinesulfonyl]-4-(2-ethoxy-2-phenylethyl)piperazine [referred to as "Compound (21)"];

1-[4-(N-isobutyl-N-cyclohexylamino)-6-quinazolinesulfonyl]-4-(2-ethoxy-2-phenylethyl)piperazine [referred to as "Compound (22)"];

1-[4-(N-methylanilino)-6-quinazolinesulfonyl]-4-(2-ethoxy-2-phenylethyl)-piperazine [referred to as "Compound (23)"];

1-[4-(N-ethylanilino)-6-quinazolinesulfonyl]-4-(2-ethoxy-2-phenylethyl)-piperazine [referred to as "Compound (24)"];

1-[4-(N-methyl-N-benzylamino)-6-quinazolinesulfonyl]-4-(2-ethoxy-2-phenylethyl)piperazine [referred to as "Compound (25)"];

1-[4-(N-methyl-N-cyclohexylamino)-6-quinazolinesulfonyl]-4-(2-methoxy-2-phenylethyl)piperazine [referred to as "Compound (26)"];

1-[4-(N-methyl-N-cyclohexylamino)-6-quinazolinesulfonyl]-4-(2-isopropoxy-2-phenylethyl)piperazine [referred to as "Compound (27)"];

1-[4-(N-methyl-N-cyclohexylamino)-6-quinazolinesulfonyl]-4-(2-isobutoxy-2-phenylethyl)piperazine [referred to as "Compound (28)"];

N-(2-aminoethyl)-4-piperidino-6-quinazolinesulfonamide [referred to as "Compound (29)"];

N-(3-aminopropyl)-4-piperidino-6-quinazolinesulfonamide [referred to as "Compound (30)"];

N-(4-aminobutyl)-4-piperidino-6-quinazolinesulfonamide [referred to as "Compound (31)"];

N-(6-aminohexyl)-4-piperidino-6-quinazolinesulfonamide [referred to as "Compound (32)"];

N-(10-aminodecyl)-4-piperidino-6-quinazolinesulfonamide [referred to as "Compound (33)"];

N-(4-aminobutyl)-4-(1-pyrrolidinyl)-6-quinazolinesulfonamide [referred to as "Compound (34)"];

N-(4-aminobutyl)-4-dimethylamino-6-quinazolinesulfonamide [referred to as "Compound (35)"];

N-(4-aminobutyl)-4-diethylamino-6-quinazolinesulfonamide [referred to as "Compound (36)"];

N-(4-aminobutyl)-4-dibutylamino-6-quinazolinesulfonamide [referred to as "Compound (37)"];

N-(4-aminobutyl)-4-dihexylamino-6-quinazolinesulfonamide [referred to as "Compound (38)"]; and the pharmaceutically acceptable acid addition salts thereof.

The acid addition salts of the 6-quinazolinesulfonyl derivatives of Formula (I) according to this invention are pharmaceutically acceptable non-toxic salts and can be prepared by conventional methods.

Suitable examples of such pharmaceutically acceptable acid addition salts include the salts of inorganic acids such as hydrochloric acid, hydrobromic acid, phosphoric acid and sulfuric acid; and the salts of organic acids such as acetic acid, citric acid, tartaric acid, lactic acid, succinic acid, fumaric acid, maleic acid, methanesulfonic acid and p-toluenesulfonic acid.

The 6-quinazolinesulfonyl derivatives of Formula (I) of this invention can be prepared by reacting a 4-substituted-6-quinazoline-sulfonyl halide of Formula (II);

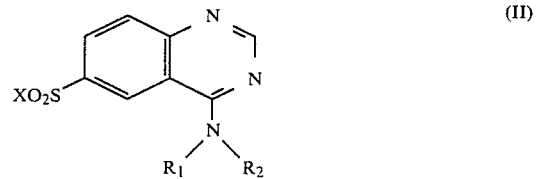

wherein $R_1$ is a hydrogen atom or a $C_{1-12}$ alkyl group;

$R_2$ is a hydrogen atom, a $C_{1-12}$ alkyl group, a $C_{4-10}$ cycloalkyl group, an aryl group or an aralkyl group; and $R_1$ and $R_2$ may be linked directly or through an oxygen atom to form a 5- to 7-membered heterocyclic ring together with the adjacent nitrogen atom; and X is a halogen atom such as chlorine atom and a bromine atom, with a compound of Formula (III);

$R_3H$         (III)

wherein $R_3$ is a

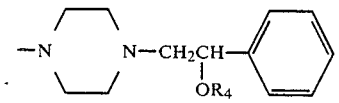

group wherein $R_4$ is a $C_{1-8}$ alkyl group; a —$HN(CH_2)_nNH_2$ group wherein n is an integer of 2 to 10; or a

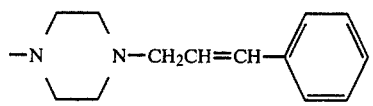

group,
in accordance with the following equation:

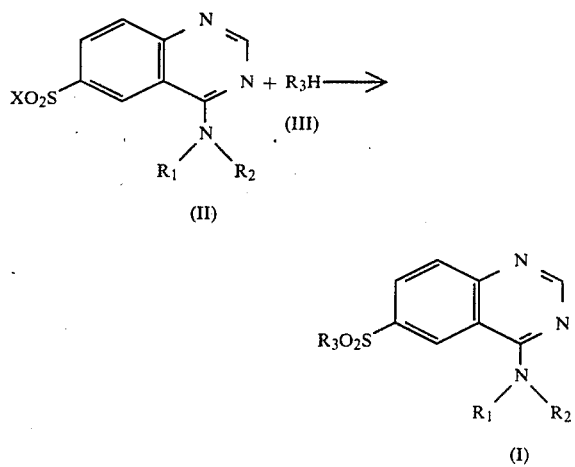

The compound of Formula (II) which is a novel compound can be prepared by reacting a sulfonic acid corresponding to the 4-substituted-6-quinazolinesulfonyl halide of Formula (II) with a halogenating agent by conventional methods.

Exemplary halogenating agents which can be employed include phosphorus pentachloride, phosphorus tribromide, phosphorus trichloride, thionyl chroride, phosphorus oxychloride and chlorosulfonic acid.

In a preferred method the compound of Formula (II) can be prepared by heating the sulfonic acid corresponding to the 4-substituted-6-quinazolinesulfonyl halide of Formula (II) with about 5 to about 10 mols of chlorosulfonic acid per mol of the sulfonic acid and about 0.5 to about 2 mols of phosphorus pentachloride per mol of the sulfonic acid typically at a temperature of about 100° C. to about 200° C. and preferably from 140° C. to about 170° C. for about 15 to about 48 hours.

The compounds of Formula (III) which can be employed include 1-substituted piperazines represented by the formulae

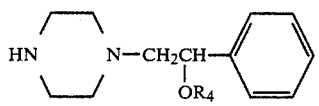

wherein $R_4$ is a $C_{1-8}$ alkyl group and

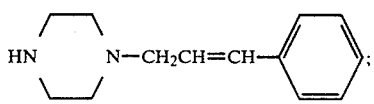

and 1,ω-diaminoalkanes represented by the formula $H_2N(CH_2)_nNH_2$ wherein n is an integer of 1 to 10. Exemplary 1-substituted piperazines include 1-(2-alkoxy-2-phenylethyl)piperazines such as 1-(2-methoxy-2-phenylethyl)piperazine, 1-(2-ethoxy-2-phenylethyl)piperazine, 1-(2-n-propoxy-2-phenylethyl)piperazine, 1-(2-isopropoxy-2-phenylethyl)piperazine, 1-(2-n-butoxy-2-phenylethyl)-piperazine and 1-(2-isobutoxy-2-phenylethyl)piperazine; and 1-cinnamylpiperazine. Exemplary 1,ω-diaminoalkanes include 1,2-diaminoethane, 1,3-diaminopropane, 1,4-diaminobutane, 1,5-diaminopentane, 1,6-diaminohexane, 1,8-diaminooctane and 1,10-diaminodecane.

The reaction between the compound of Formula (II) and the compound of Formula (III) can be carried out in the presence or absence of an acid acceptor. Exemplary acid acceptors which can be employed include alkali metal compounds such as sodium bicarbonate, sodium carbonate, potassium carbonate, sodium hydroxide, potassium hydroxide, sodium hydride and sodium alkoxides such as sodium methoxide, sodium ethoxide and sodium tert-butoxide; and organic tertiary amines such as trimethylamine, triethylamine and 1,4-diazabicyclo[2,2,2]octane.

In general, this reaction is carried out in the presence of a reaction medium. Exemplary reaction media which can be employed include halogenated hydrocarbons such as chloroform and dichloroethane; alcohols such as methanol, ethanol and butanol; ethers such as tetahydrofuran and dioxane; N,N-dimethylformamide, dimethyl sulfoxide, acetonitrile and water. The reaction media may be used singly or in combination with one another.

The amount of the compound of Formula (III) which can be employed is at least about 1 mol and typically ranges from about 1 to about 10 mols, preferably from 1.0 to 5 mols per mol of the compound of Formula (II). A more preferred amount of the compound of Formula (III) ranges from 1.0 to 3.0 mols per mol of the compound of Formula (II) when the acid acceptor is present, and from 2.0 to 5.0 mols per mol of the compound of Formula (II) when the acid acceptor is absent.

The amount of the acid acceptor employed is preferably about 1 to about 10 equivalents and more preferably 1 to 6 equivalents for each mol of the compound of Formula (III).

The reaction between the compound of Formula (II) and the compound of Formula (III) can be carried out typically at a temperature of from about −30° C. to about 150° C. and preferably from about 0° C. to about 30° C.

While this reaction can be carried out at a pressure above atmospheric, it is generally advisable to utilize atmospheric pressure for practical purposes.

The reaction time which can be employed is typically about 0.5 to about 48 hours and preferably about 0.5 to 20 hours at atmospheric pressure.

Also, the 6-quinazolinesulfonyl derivatives of Formula (I) of this invention can be prepared by reacting a 4-halogeno-6-quinazolinesulfonyl derivatives of Formula (IV):

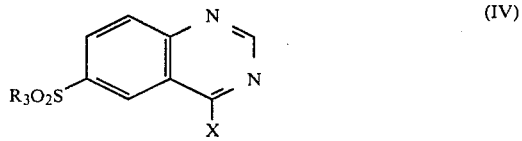

wherein
R₃ is a

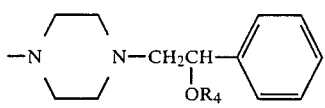

group wherein R₄ is a $C_{1-8}$ alkyl group; a $-HN(CH_2)_nNH_2$ group wherein n is an integer of 2 to 10; or a

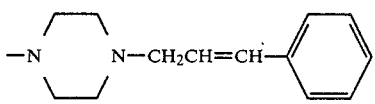

group; and
X is a halogen atom such as a chlorine atom and a bromine atom,
with an amine of Formula (V):

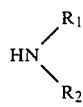   (V)

wherein
$R_1$ is a hydrogen atom or a $C_{1-12}$ alkyl group;
$R_2$ is a hydrogen atom, a $C_{1-12}$ alkyl group, a $C_{4-10}$ cycloalkyl group, an aryl group or an aralkyl group; and
$R_1$ and $R_2$ may be linked directly or through an oxygen atom to form a 5- to 7-membered heterocyclic ring together with the adjacent nitrogen atom,
in accordance with the following equation:

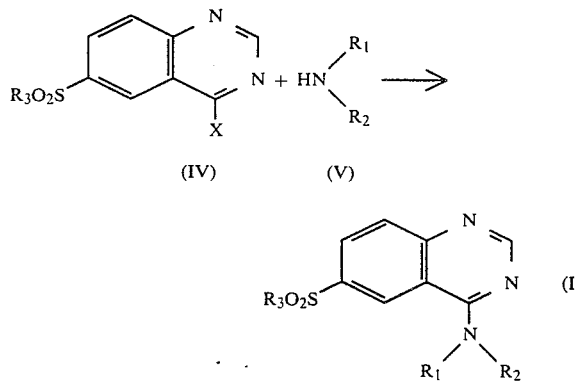

The compound of Formula (IV) which is a novel compound can be prepared by reacting 3,4-dihydro-4-oxo-6-quinazolinesulfonyl chloride or bromide with the same compound of Formula (III) as described above to give a 3,4-dihydro-4-oxo-6-quinazolinesulfonyl derivative of Formula (VI):

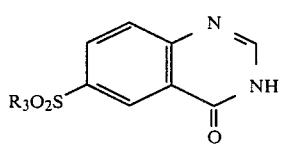   (VI)

and reacting the 3,4-dihydro-4-oxo-6-quinazolinesulfonyl derivative with a halogenating agent.

In a preferred method, 3,4-dihydro-4-oxo-6-quinazolinesulfonyl chloride is reacted with about 1 to about 2 mols of, for example, a 1-(2-alkoxy-2-phenylethyl)piperazine per mol of the 3,4-dihydro-4-oxo-6-quinazolinesulfonyl chloride in the presence of about 1 to about 5 mols of anhydrous potassium carbonate per mol of the 3,4-dihydro-4-oxo-6-quinazolinesulfonyl chloride in a reaction medium such as chloroform at a temperature of from about 10° C. to about 30° C. for a reaction time of from about 0.5 to about 20 hours to give a 3,4-dihydro-4-oxo-6-quinazolinesulfonyl derivative of Formula (VI). Then the 3,4-dihydro-4-oxo-6-quinazolinesulfonyl derivative of Formula (VI) which is a novel compound is heated with a halogenating agent in the presence or absence of an inert reaction medium. Exemplary halogenating agents include thionyl chloride, phosphorus oxychloride, phosphorus trichloride, phosphorus tribromide and phosphorus pentachloride. The amount of the halogenating agent used is not particularly limited and preferably ranges from about 3 to about 30 mols per mol of the 3,4-dihydro-4-oxo-6-quinazolinesulfonyl derivative of Formula (VI) in the absence of an inert reaction medium and preferably ranges from about 3 to 8 mols per mol of the 3,4-dihydro-4-oxo-6-quinazolinesulfonyl derivative of Formula (VI) in the presence of an inert reaction medium. Exemplary inert reaction media include N,N-dimethylformamide, chloroform, benzene and toluene. The heating temperature typically ranges from about 20° C. to about 200° C., preferably from about 60° C. to about 150° C. and more preferably from about 70° C. to about 120° C. A more preferred halogenation is conducted by heating the 3,4-dihydro-4-oxo-6-quinazolinesulfonyl derivative of Formula (VI) with about 20 to about 30 mols of thionyl chloride in the presence of about 5 to about 15% by volume of N,N-dimethylformamide at about 80° C. for about 0.5 to about 1 hour.

Exemplary amines of Formula (V) which can be employed in the reaction between the 4-halogeno-6-quinazolinesulfonyl derivative of Formula (IV) and the amine of Formula (V) include ammonia, dimethylamine, diethylamine, di-n-propylamine, diisopropylamine, di-n-butylamine, diisobutylamine, di-n-hexylamine, cyclopentylamine, cyclohexylamine, cycloheptylamine, aniline, benzylamine, phenethylamine, N-methylcyclopentylamine, N-methyl-N-cyclohexylamine, N-methyl-N-cyclohexylamine, N-methyl-N-cycloheptylamine, N-ethyl-N-cyclohexylamine, N-n-propyl-N-cyclohexylamine, N-isobutyl-N-cyclohexylamine, N-methylaniline, N-ethylaniline, N-butylaniline, N-methyl-N-benzylamine, N-methyl-N-phenethylamine, pyrrolidine, piperidine and morpholine, and the acid addition salts thereof such as the hydrochlorides.

The reaction between the 4-halogeno-6-quinazoline derivative of Formula (IV) and the amine of Formula (V) can be carried out in the presence or absence of an acid acceptor. Exemplary acid acceptors employed include the same acceptors as employed in the reaction between the compound of Formula (II) and the compound of Formula (III).

In general, the reaction between the 4-halogeno-6-quinazoline derivative of Formula (IV) and the amine of Formula (V) is carried out in the presence of a reaction medium. Exemplary reaction media employed include the same reaction media as employed in the reaction between the compound of Formula (II) and the compound of Formula (III).

The amount of the amine of Formula (V) which can be employed is at least about 1 mol and typically ranges from about 1 to about 20 mols, preferably from 1.2 to 10 mols per mol of the 4-halogeno-6-quinazolinesulfonyl derivative of Formula (IV). A more preferred amount of the amine of Formula (V) ranges from 1.2 to 6 mols per mol of the 4-halogeno-6-quinazolinesulfonyl derivative of Formula (IV) when the acid acceptor is present, and from 2.0 to 6.0 mols per mol of the 4-halogenoquinazolinesulfonyl derivative of Formula (IV) when the acid acceptor is absent.

The amount of the acid acceptor employed is preferably about 1 to about 10 equivalents and more preferably 1 to 4 equivalents for each mol of the compound of Formula (V).

The reaction between the 4-halogeno-6-quinazolinesulfonyl derivative of Formula (IV) and the amine of Formula (V) can be carried out typically at a temperature of from about $-30°$ C. to about $150°$ C. and preferably from about $0°$ C. to about $60°$ C.

While this reaction can be carried out at a pressure above atmospheric, it is generally advisable to utilize atmospheric pressure for practical purposes.

The reaction time which can be employed is typically about 0.5 to about 48 hours and preferably about 0.5 to about 20 hours at atmospheric pressure.

The method of separating and extracting the 6-quinazolinesulfonyl derivative of Formula (I) from the reaction solution comprises extracting the compound of Formula (I) with diluted hydrochloric acid to render it basic, extracting the extract with a solvent such as chloroform capable of easily dissolving the extract, condensing the extract and subjecting the condensed residues to a silica gel-column or aluminum-column chromatography for purification.

It has now been found that the 6-quinazolinesulfonyl derivatives of Formula (I) and the pharmaceutically acceptable salts have pharmacologically and biochemically interesting properties such as a relaxatory action for vascular smooth muscle and an inhibitory action for phosphodiesterase and are useful as a vasodilator, a hypotensor, an ameliorant of cerebral circulation, a medicine for angina pectoris and a preventive and a medicine for cardiovascular thrombosis.

More specifically, from the results of the experiment using an enzyme specimen in accordance with the reports [*Mol. Pharmacol.*, 15, 49 (1979) and *Biochem. Biophys. Res. Comun.*, 84, 277 (1978)], it has been found that the 6-quinazolinesulfonyl derivatives and the pharmaceutically acceptable acid addition salts of this invention can inhibit an enzyme, i.e., phosphodiesterase (abbreviated "PDE") which decomposes adenosine-3',5'-monophosphate (abbreviated "c-AMP"), and also can inactivate calmodulin or calcium dependent cyclic nucleotide phosphodiesterase. The 6-quinazolinesulfonyl derivatives and the pharmaceutically acceptable acid addition salts have inhibited the decomposition due to the enzyme specimens of substrate c-AMP and guanosine-3',5'-monophosphate (abbreviated "c-GMP"). This means that the compounds of this invention can inhibit the decomposition of the c-AMP and maintain the c-AMP in tissue at a high concentration. In other words, the compounds of this invention are effective for the improvement and medical treatment of a disease accompanied by reduction in the c-AMP and a disease accompanied by infiltration of calcium into tissue, for example, the contraction and convulsion of vascular smooth muscle.

The effect of the 6-quinazolinesulfonyl derivatives and the pharmaceutically acceptable acid addition salts of this invention on smooth muscle can be proved by suspending a mesenteric artery taken out from a rabbit in a helical form, contracting the mesenteric artery with potassium chloride and adding the 6-quinazolinesulfonyl derivatives or their pharmaceutically acceptable acid addition salts of this invention to the contracted mesenteric artery, resulting in the relaxation of the mesenteric artery. When, for example, 1-[4-(N-methyl-N-cyclohexylamino)-6-quinazolinesulfonyl]-4-(2-ethoxy-2-phenylethyl)piperazine was added and a complete relaxation was designated 100%, the concentration which could bring about a relaxation of 50%, i.e., $ED_{50}$ was 0.8 $\mu M$.

The effect of the 6-quinazolinesulfonyl derivatives and the pharmaceutically acceptable acid addition salts of this invention on the vasodilation of the femoral and vertebral arteries can be measured by anesthetizing a dog of mixed breed weighing 8 to 15 Kg by an intravenous administration of 35 mg/Kg of pentbarbital, providing an acute type probe (a product of Nippon Koden K.K., Japan) with the femoral and vertebral arteries, administering the 6-quinazolinesulfonyl derivatives and the pharmaceutically acceptable acid addition salts to the femoral vein through a polyethylene tube inserted into the femoral vein side chain and measuring the blood flow volume with an electromagnetic flowmeter (a product of Nippon Koden K.K., Japan, "MF-27"). For example, when 1 mg/Kg of 1-[4-(N-methyl-N-cyclohexylamino)-6-quinazolinesulfonyl]-4-(2-ethoxy-2-phenylethyl)piperazine was intravenously administered, the increased blood flow volume in the femoral artery was 33% and the increased blood flow volume in the vertebral artery was 59%.

Furthermore, when the 6-quinazolinesulfonyl derivatives and the pharmaceutically acceptable acid addition salts of this invention are intravenously and arterially administered for the above described purposes, any remarkable toxicity cannot be observed. For example, the acute toxicity of 1-[4-(N-methyl-N-cyclohexylamino)-6-quinazolinesulfonyl]-4-(2-ethoxy-2-phenylethyl)piperazine, i.e., $LD_{50}$ was 63 mg/Kg in giving male ddY-strain mice an intravenous administration.

The following examples illustrate the present invention in more detail, but they are given for illustrative purposes only and are not to be construed as limiting the invention.

REFERENTIAL EXAMPLE 1

Syntheses of 4-Substituted-6-Quinazolinesulfonyl Chlorides

In a mixture of 18.1 ml of chlorosulfonic acid and 5.4 g of phosphorus pentachloride was gradually added 8.6 g of 4-piperidinoquinazoline, and the mixture was heated at $150°$ C. for 20 hours. The reaction solution was poured into 200 g of a mixture of ice and water and extracted with chloroform. The chloroform layer was washed with water, then with a saturated sodium bicarbonate solution, and dried with Glauber's salt. The chloroform layer thus obtained was condensed under reduced pressure to give 6.0 g of 4-piperidino-6-quinazolinesulfonyl chloride as an oily substance.

Mass spectrum (m/e): 313, 311($M^+$), 276.

NMR spectrum (CDCl₃): 8.7(1H, singlet, 2nd position hydrogen), 7.95(1H, doublet, 8th position hydrogen, $J_{8-7}=9$ Hz), 8.58 (1H, doublet, $J_{5-7}=2$ Hz) and 8.36(1H, doublet-doublet, 7th position, $J_{5-7}=2$ Hz, $J_{8-7}=9$ Hz).

The above described procedures were repeated except that 4-(1-pyrrolidinyl)quinazoline, 4-dimethylaminoquinazoline, 4-diethylaminoquinazoline, 4-dibutylaminoquinazoline and 4-dihexylaminoquinazoline in an amount equimolar to 8.6 g of 4-piperidinoquinazoline were employed instead of the 8.6 g of 4-piperidinoquinazoline, respectively, and the 4-substituted-6-quinazolinesulfonyl chlorides as set forth in Table 1 were obtained.

TABLE 1

| Substituent in 4th Position | Mass Spectrum (m/e) |
| --- | --- |
| 4-(1-Pyrrolidinyl) | 297, 299(M⁺), 262 |
| 4-Dimethylamino | 271, 273(M⁺), 236 |
| 4-Diethylamino | 299, 301(M⁺), 264 |
| 4-Dipropylamino | 327, 329(M⁺), 292 |
| 4-Dibutylamino | 355, 357(M⁺), 320 |
| 4-Dihexylamino | 411, 413(M⁺), 376 |

REFERENTIAL EXAMPLE 2

Synthesis of 1-(4-Chloro-6-quinazolinesulfonyl)-4-(2-ethoxy-2-phenylethyl)piperazine In 200 ml of chloroform was dissolved 11.7 g of 1-(2-ethoxy-2-phenylethyl)piperazine, and then 6.9 g of anhydrous potassium carbonate was added thereto. To the solution thus obtained was added dropwise 100 ml of a chloroform solution containing 12.2 g of 3,4-dihydro-4-oxo-6-quinazolinesulfonyl chloride under cooling with ice. After the dropwise addition of the chloroform solution, the mixed solution was stirred at a temperature of 20° C. to 25° C. for 15 hours, and then added with 50 ml of water. After the pH of the reaction solution was adjusted to 7, the chloroform layer was separated therefrom and the aqueous layer was further extracted with chloroform and the chloroform layer obtained was combined with the one previously separated. Then the chloroform layer was washed with water, dried with Glauber's salt and condensed under reduced pressure to give an oily substance. To this oily substance were added 50 ml of ethanol and 10 ml of conc. hydrochloric acid to form a solution, and the solution was condensed to dryness and the residue was recrystallized from ethanol and then from ether to give 18.2 g of 1-(3,4-dihydro-4-oxo-6-quinazolinesulfonyl)-4-(2-ethoxy-2-phenylethyl)piperazine hydrochloride having a melting point (decomposition) of 249° C. to 250° C. in a yield of 76%.

Mass spectrum (m/e): 442(M⁺), 398, 382 and 307.

NMR spectrum (δ, CDCl₃): 1.0(3H), 2.2~3.3(10H), 3.0~3.3(2H), 4.3(1H), 7.2(5H), 7.8(2H), 8.3(1H) and 8.5(1H).

IR absorption spectrum ($\nu_{max}^{KBr}$, cm⁻¹): 1720(c=o)

To 9.57 g of 1-(3,4-dihydro-4-oxo-6-quinazolinesulfonyl)-4-(2-ethoxy-2-phenylethyl)piperazine hydrochloride were added 40 ml of thionyl chloride and 4.8 ml of N,N-dimethylformamide, and the mixture was refluxed under heating. To the residue thus obtained were added 60 ml of chloroform and 30 ml of a mixture of ice and water, and the mixture was stirred under cooling with ice. Then the chloroform layer was separated therefrom and the aqueous layer was extracted with chloroform and the chloroform layer obtained was combined with the one previously separated. The chloroform layer was washed with, in order, water, a saturated sodium bicarbonate solution and water, and then dried with Glauber's salt. The chloroform layer thus obtained was condensed under reduced pressure to give 7.33 g of 1-(4-chloro-6-quinazolinesulfonyl)-4-(2-ethoxy-2-phenylethyl)piperazine as an oily substance in a yield of 80%.

In the same manner as described above there were obtained 1-(4-chloro-6-quinazolinesulfonyl)-4-(2-methoxy-2-phenylethyl)piperazine, 1-(4-chloro-6-quinazolinesulfonyl)-4-(2-isopropoxy-2-phenylethyl)piperazine and 1-(4-chloro-6-quinazolinesulfonyl)-4-(2-isobutoxy-2-phenylethyl)piperazine using the reaction conditions as set forth in Tables 2-1 and 2-2.

TABLE 2-1

| Run No. | ClO₂S—(quinazoline-NH) (g) | CHCH₂—N(piperazine)NH, R₄ | (g) | Anhydrous K₂CO₃ (g) | Reaction Medium CHCl₃ (ml) |
| --- | --- | --- | --- | --- | --- |
| 1 | 3.7 | —CH₃ | 3.3 | 2.0 | 100 |
| 2 | 4.4 | —iC₃H₇ | 4.5 | 2.5 | 150 |
| 3 | 3.9 | —iC₄H₉ | 3.7 | 1.9 | 100 |

| Run No. | Reaction Temperature (°C.) | Reaction Time (hour) | Yield [g (%)] 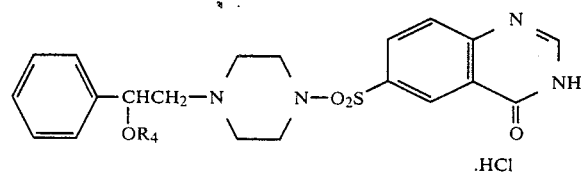 .HCl |
| --- | --- | --- | --- |
| 1 | 20~25 | 5 | 5.5 (78) |
| 2 | " | 15 | 5.6 (63) |
| 3 | " | 24 | 4.7 (67) |

TABLE 2-2

[Structure: phenyl-CH(OR4)-CH2-N(piperazine)N-O2S-(quinazoline with NH and C=O).HCl]

| Run No. | R4 | (g) | .HCl | SOCl2 (g) | N,N-Di-methyl-formamide (ml) | Reaction Temperature (°C.) | Reaction Time (hour) | Compound of Formula (IV) Yield [g (%)] |
|---|---|---|---|---|---|---|---|---|
| 1 | —CH3 | 4.8 | | 20 | 2 | reflux | 1 | 3.9 (85) |
| 2 | —iC3H7 | 4.9 | | " | " | " | " | 3.5 (75) |
| 3 | —iC4H9 | 5.1 | | " | " . | " | " | 3.3 (66) |

EXAMPLE 1

In 100 ml of chloroform was dissolved 4.4 g of 1,4-diaminobutene, and to the solution was added dropwise 50 ml of a chloroform solution containing 3.1 g of 4-piperidino-6-quinazolinesulfonyl chloride under cooling with ice. After the dropwise addition of the chloroform solution, the mixed solution was stirred at a temperature of 20° C. to 25° C. for two hours, and the reaction solution was extracted with a 10% aqueous hydrochloric acid solution. The chloroform layer was washed with water and dried with anhydrous potassium carbonate. Then chloroform was distilled from the chloroform layer, and the residue was separated by Prep LC/System 500 (Waters Associates, U.S.A.) [column: Prepack 500/$C_{18}$; solvent: $H_2O$/$CH_3CN$=85/15 (volume ratio); flow rate: 100 ml/minute] to give 2.8 g of N-(4-aminobutyl)-4-piperidino-6-quinazolinesulfonamide [i.e. Compound(31)] as an oily substance in a yield of 77%.

Mass spectrum (m/e): 363($M^+$) and 305.

NMR spectrum ($CDCl_3$): 1.5~2.3(10H, 5×$CH_2$), 2.95(4H, 2×N$CH_2$), 3.3(4H, 2×N$CH_2$) and 7.83~8.83(4H).

IR absorption spectrum ($\nu_{max}^{cap}$, $cm^{-1}$): 1330 and 1160.

The same procedures as described above were repeated using the compounds of Formula (III) as set forth in Table 3-1 under the reaction conditions as set forth Table 3-1, and N-(ω-aminoalkyl)-4-substituted-6-quinazolinesulfamides as set forth in Table 3-2 were obtained. The analytical values of these compounds are shown in Table 3-2.

TABLE 3-1

Compound of Formula (II) where X is Cl and —N(R1)(R2) group

| Run No. | is shown below | Compound of Formula (III) (g) | $H_2N(CH_2)_nNH_2$ n | (g) | Reaction Temperature (°C.) | Reaction Time (hour) |
|---|---|---|---|---|---|---|
| 1 | —N(piperidine) | 3.1 | 2 | 6 | 0~5 | 3 |
| 2 | " | " | 3 | 3.7 | " | 2 |
| 3 | " | " | 6 | 5.8 | " | " |
| 4 | " | " | 10 | 8.6 | " | 10 |
| 5 | —N(pyrrolidine) | 3.0 | 4 | 8.8 | " | 2 |
| 6 | —N(CH3)2 | 2.7 | " | " | " | " |
| 7 | —N(C2H5)2 | 2.6 | " | " | " | " |
| 8 | —N(C4H9)2 | 3.3 | " | 13.2 | " | 5 |
| 9 | —N(C6H13)2 | 3.8 | " | 13.2 | " | " |

TABLE 3-2

6-Quinazolinesulfonyl Derivative of Formula (I) with —N(R1)(R2)

| Run No. | Compound Nos. | R3 | R1/R2 | Yield [g (%)] | Mass Spectrum | IR Absorption Spectrum ($\nu SO_2$, $cm^{-1}$) | NMR Spectrum ($CDCl_3$) |
|---|---|---|---|---|---|---|---|
| 1 | 29 | —NH($CH_2$)$_2$$NH_2$ | —N(piperidine) | 2.5 (75) | 335($M^+$), 305, 213, 211 | 1330, 1160 | 1.5~2.3(6H), 2.83~3.5(4H), 4.0~4.66(4H), 7.76~8.83(4H) |

TABLE 3-2-continued

| Run No. | Compound Nos. | 6-Quinazolinesulfonyl Derivative of Formula (I) R3 | —N<R1,R2 | Yield [g (%)] | Mass Spectrum | IR Absorption Spectrum (νSO2, cm⁻¹) | NMR Spectrum (CDCl3) |
|---|---|---|---|---|---|---|---|
| 2 | 30 | —NH(CH2)3NH2 | " | 2.4 (69) | 349(M+), 320 305, 275, 211 | 1330, 1160 | 1.5~2.3(8H), 2.83~3.5(4H) 4.0~4.6(4H), 7.56~8.9(4H) |
| 3 | 32 | —NH(CH2)6NH2 | " | 3.2 (81) | 391(M+), 362 305, 211 | 1330, 1160 | 1.5~2.3(14H), 2.83~3.5(4H) 4.1~4.7(4H), 7.8~8.9(4H) |
| 4 | 33 | —NH(CH2)10NH2 | " | 2.5 (56) | 447, 428, 404 389, 375, 361 305 | 1330, 1165 | 1.18(16H), 1.8(6H) 2.4~3.5(7H), 3.8(4H) 7.9~8.7(4H) |
| 5 | 34 | —NH(CH2)4NH2 | 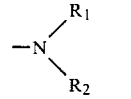 | 2.7 (77) | 349, 291 | 1330, 1160 | 1.22~1.73(4H), 2.1(4H) 2.56~3.22(4H), 3.7~4.1(4H), 8.11~9.03(4H) |
| 6 | 35 | " | —N(CH3)2 | 2.6 (81) | 323, 265 | 1330, 1160 | 1.7~2.0(4H), 3.1(6H, 2 × CH3) 2.8~3.2(4H), 7.5~8.8(4H) |
| 7 | 36 | " | —N(C2H5)2 | 2.5 (83) | 351, 322, 305 | 1330, 1160 | 1.0~2.0(10H), 2.3~3.1(4H) 3.55(2H, NH2), 3.6~4.1(4H) 7.8~8.7(4H) |
| 8 | 37 | " | —N(C4H9)2 | 2.8 (74) | 407, 350 | 1330, 1160 | 0.5~2.1(18H, 2 × CH3 + 6 × CH2) 2.2~3.1(4H), 3.3~4.1(4H) 7.5~8.73(4H) |
| 9 | 38 | " | —N(C6H13)2 | 2.7 (66) | 463, 272 | 1340, 1165 | 0.5~2.3(26H, 2 × CH3 + 10 × CH2) 2.2~3.3(4H), 3.3~4.1(4H) 7.5~8.7(4H) |

EXAMPLE 2

To 300 ml of chloroform saturated with ammonia was added 4.61 g of 1-(4-chloro-6-quinazolinesulfonyl)-4-(2-ethoxy-2-phenylethyl)piperazine, and the mixture was stirred at a temperature of 20° C. to 25° C. for 15 hours. The reaction solution was washed with water and then condensed. The residue thus obtained was subjected to the same silica gel-column chromatography as in Example 1 using chloroform as the solvent to give 3.40 g of 1-(4-amino-6-quinazolinesulfonyl)-4-(2-ethoxy-2-phenylethyl)piperazine [i.e., Compound (1)] in a yield of 77%.

Mass spectrum (m/e): 441 and 306.

NMR spectrum (CDCl3): 1.1(3H), 2.5~3.3(10H), 3.2~3.4(2H), 4.2(1H), 7.2(5H) and 7.9~8.8(4H).

1-(4-Amino-6-quinazolinesulfonyl)-4-(2-ethoxy-2-phenylethyl)piperazine.2HCl.

Melting point: 195°~200° C.

IR absorption spectrum ($\nu_{max}^{KBr}$, cm⁻¹): 3400, 3070, 1620, 1380, 1365 and 1175.

EXAMPLE 3

In 100 ml of chloroform was dissolved 4.61 g of 1-(4-chloro-6-quinazolinesulfonyl)-4-(2-ethoxy-2-phenylethyl)piperazine, and then 4.14 g of anhydrous potassium carbonate and 4.9 g of dimethylamine hydrochloride, and the mixture thus obtained was stirred at a temperature of 20° C. to 25° C. for 15 hours. The reaction solution was filtered and the filtrate was washed with chloroform, then with water, dried with Glauber's salt, and chloroform was distilled therefrom. The residue thus obtained was subjected to the same silica gel-column chromatography as in Example 1 using chloroform as the solvent to give 3.71 g of 1-(4-dimethylamino-6-quinazolinesulfonyl)-4-(2-ethoxy-2-phenylethyl)piperazine [i.e., Compound (2)] in a yield of 79%.

Mass spectrum (m/e): 469, 425, 410 and 334.

NMR spectrum (CDCl3): 1.0(3H), 2.2~3.3(10H), 3.0~3.4(2H), 3.2(6H), 4.3(1H), 7.2(5H) and 7.8~8.5(4H).

1-(4-Dimethylamino-6-quinazolinesulfonyl)-4-(2-ethoxy-2-phenylethyl)piperazine.2HCl.

Melting point: 153°~155° C. (decomp.).

IR absorption spectrum ($\nu_{max}^{KBr}$, cm⁻¹): 3420, 1610, 1570, 1385 and 1170.

The same procedures as described above were repeated except that 6.6 g of diethylamine hydrochlide was employed instead of the 4.9 g of dimethylamine hydrochloride and there was obtained 1-(4-diethylamino-6-quinazolinesulfonyl)-4-(2-ethoxy-2-phenylethyl)piperazine [i.e., Compound (3)] in a yield of 81%.

Mass spectrum (m/e): 497, 453 and 362.

NMR spectrum (CDCl3): 1.0(9H), 2.2~3.8(14H), 4.4(1H), 7.2(5H) and 7.8~8.5(4H).

EXAMPLE 4

In 50 ml of chloroform was added 4.61 g of 1-(4-chloro-6-quinazolinesulfonyl)-4-(2-ethoxy-2-phenylethyl)piperazine, and to the solution was added 1.7 g, and the mixture was stirred at a temperature of 20° C. to 25° C. for 30 minutes. The reaction solution was washed with water and the then chloroform was distilled therefrom. The residue thus obtained was subjected to the same silica gel-column chromatography as in Example 1 using chloroform as the solvent to give 4.43 g of 1-(4-piperidino-6-quinazolinesulfonyl)-4-(2-ethoxy-2-phenylethyl)piperazine [i.e., Compound (6)] in a yield of 87%.

Mass spectrum (m/e): 509(M+), 465, 451 and 375.

NMR spectrum (CDCl3): 1.0(3H), 1.8(6H), 2.2~3.3(10H), 3.0~3.4(2H), 3.8(4H), 4.3(1H), 7.2(5H) and 7.9~8.5(4H).

1-(4-Piperidino-6-quinazolinesulfonyl)-4-(2-ethoxy-2-phenylethyl)piperazine.2HCl.

Melting point: 190°~191° C. (decomp.)

IR absorption spectrum ($v_{max}^{KBr}$, cm$^{-1}$): 1610, 1560, 1370 and 1170.

The same procedures as described above were repeated using the compounds of Formula (IV) and the amines of Formula (V) as set forth in Table 4-1 under the reaction conditions as set forth in Table 4-1. The analytical values of the 6-quinazolinesulfonyl derivatives of Formula (I) thus obtained are shown in Table 4-2.

form was distilled therefrom. The residue was subjected to the same silica gel-column chromatography as in Example 1 using chloroform as the solvent for purification to give 4.2 g of 1-[4-(N-methyl-N-cyclohexylamino)-6-quinazolinesulfonyl]-4-(2-ethoxy-2-phenylethyl)piperazine [i.e., Compound (19)] in a yield of 79%.

Mass spectrum (m/e): 538, 537, 492, 403 and 320.

NMR spectrum (CDCl$_3$): 0.66~2.33(13H), 2.33~3.7(16H), 4.1~4.6(1H), 7.2(5H) and 7.8~8.8(4H).

TABLE 4-1

| Run No. | Compound of Formula (IV) where X is Cl and R$_3$ is —N(piperazinyl)N—CH$_2$CH(OR$_4$)—phenyl group wherein R$_4$ is shown below (g) | | Amine of Formula (V) (g) | Reaction Medium (ml) | Reaction Temperature (°C.) | Reaction Time (hour) |
|---|---|---|---|---|---|---|
| 1 | —CH$_3$ | 3.40 | HN(piperidine) 1.44 | CHCl$_3$ 40 | 20~25 | 1 |
| 2 | —C$_2$H$_5$ | 2.19 | HN(morpholine) 1.24 | CHCl$_3$ 30 | " | 2 |
| 3 | " | 4.61 | HN(C$_4$H$_9$)$_2$ 2.84 | CHCl$_3$ 50 | " | 5 |

TABLE 4-2

| Run No. | Compound No. | 6-Quinazolinesulfonyl Derivative of Formula (I) R$_3$ | —N(R$_1$)(R$_2$) | Yield [g (%)] | Melting Point (°C.) | Mass Spectrum | IR Absorption Spectrum ($v_{max}^{KBr}$, cm$^{-1}$) | NMR Spectrum (CDCl$_3$) |
|---|---|---|---|---|---|---|---|---|
| 1 | 5 | —N(piperazinyl)N—CH$_2$CH(OCH$_3$)—phenyl | —N(piperidinyl) | 3.12 (83) | 2HCl 166~169 | 496 | 1610, 1560 1360, 1170 (2HCl) | 1.6(6H), 2.3~3.2(10H) 3.6~3.8(4H), 3.8(3H) 4.25(1H), 7.2(5H) 7.8~8.5(4H) |
| 2 | 14 | —N(piperazinyl)N—CH$_2$CH(OC$_2$H$_5$)—phenyl | —N(morpholinyl) | 2.06 (85) | 2HCl 180~183 | 511, 466 376 | 3420, 1605 1560, 1360 1180 (2HCl) | 1.0(3H), 2.3~3.3(10H) 3.2~3.5(2H), 3.9(8H) 4.3(1H), 7.2(5H) 7.9~8.8(4H) |
| 3 | 4 | " | —N(C$_4$H$_9$)$_2$ | 3.76 (68) | 2HCl 205~208 | 554, 419 363, 335 | 3425, 1610 1560, 1360 1160 (2HCl) | 0.8~2.0(17H) 2.3~3.5(10H) 3.2~3.5(2H) 3.6(4H), 4.3(1H) 7.2(5H), 7.8~8.6(4H) |

EXAMPLE 5

In 50 ml of chloroform was dissolved 4.6 g of 1-(4-chloro-6-quinazolinesulfonyl)-4-(2-ethoxy-2-phenylethyl)piperazine, and to the solution were added 1.7 g of N-methyl-N-cyclohexylamine and 1 g of anhydrous potassium carbonate, and the mixture was stirred at a temperature of 20° C. to 25° C. for 3 hours. The reaction solution thus obtained was washed with water, dried with anhydrous potassium carbonate and then chloroform was distilled therefrom.

IR absorption spectrum ($v_{max}^{cap}$, cm$^{-1}$): 1590, 1560, 1490, 1370 and 1170.

The same procedures as described above were repeated using the compounds of Formula (IV) and the amines of Formula (V) as set forth in Table 5-1 under the reaction conditions as set forth in Table 5-1. The analytical values of the 6-quinazolinesulfonyl derivatives of Formula (I) thus obtained are shown in Table 5-2.

TABLE 5-1

| Run No. | Compound of Formula (IV) where X is Cl and R₃ is $-N\diagup\diagdown N-CH_2CH(OR_4)-C_6H_5$ group wherein R₄ is shown below (g) | | Amine of Formula (V) (g) | | Anhydrous $K_2CO_3$ (g) | Reaction Medium (ml) | Reaction Temperature (°C.) | Reaction Time (hour) |
|---|---|---|---|---|---|---|---|---|
| 1 | $-C_2H_5$ | 2.76 | HN(CH₃)-cyclopentyl | 1.2 | 1.6 | CHCl₃ 30 | 20~25 | 2 |
| 2 | " | 2.30 | HN(CH₃)-cycloheptyl | 1.3 | 1.4 | " | " | 5 |
| 3 | " | " | HN(CH₂CH(CH₃)₂)-cyclohexyl | 1.6 | " | " | " | 1.5 |
| 4 | " | 4.61 | HN(CH₃)-phenyl | 2.7 | 2.1 | CHCl₃ 50 | " | 15 |
| 5 | " | " | HN(CH₃)-CH₂-phenyl | 2.4 | 2.1 | " | " | " |
| 6 | $-CH_3$ | 1.38 | HN(CH₃)-cyclohexyl | 0.7 | 0.4 | CHCl₃ 20 | 20~25 | 3 |
| 7 | $-CH(CH_3)_2$ | 1.42 | HN(CH₃)-cyclohexyl | " | " | " | " | " |
| 8 | $-CH_2CH(CH_3)_2$ | 1.47 | HN(CH₃)-cyclohexyl | " | " | " | " | " |
| 9 | $-C_2H_5$ | 2.30 | H₂N-cyclohexyl | 1.5 | 1.0 | CHCl₃ 30 | " | " |

TABLE 5-1-continued

| | Compound of Formula (IV) where X is Cl and R₃ is | | | | | | |
|---|---|---|---|---|---|---|---|
| Run No. | −N⌒N−CH₂CH(OR₄)−C₆H₅ group wherein R₄ is shown below (g) | Amine of Formula (V) (g) | Anhydrous K₂CO₃ (g) | Reaction Medium (ml) | Reaction Temperature (°C.) | Reaction Time (hour) |
| 10 | " | " | H₂N−C₆H₅  1.4 | " | " | " | " |
| 11 | " | 1.15 | H₂NCH₂−C₆H₅  1.1 | 0.7 | CHCl₃ 20 | " | " |

TABLE 5-2

| Run No. | Compound No. | 6-Quinazolinesulfonyl Derivative of Formula (I) | | Yield [g (%)] | Mass Spectrum | IR Absorption Spectrum ($\nu_{max}^{cap}$,cm$^{-1}$) | NMR Spectrum (CDCl₃) |
|---|---|---|---|---|---|---|---|
| | | R₃ | −N(R₁)(R₂) | | | | |
| 1 | 18 | −N⌒N−CH₂CH(OC₂H₅)−C₆H₅ | −N(CH₃)(cyclopentyl) | 2.67 (85) | 523, 478, 389 306 | 1600, 1560 1480, 1370 1160 | 0.7~2.3(11H) 2.3~2.7(16H) 4.4(1H), 7.2(5H) 7.8~8.8(4H) |
| 2 | 20 | −N⌒N−CH₂CH(OC₂H₅)−C₆H₅ | −N(CH₃)(cyclohexyl) | 2.15 (78) | 552, 551, 417 333 | 1610, 1560 1490, 1370 1170 | 0.5~2.2(15H) 2.4~3.7(16H) 4.5(1H), 7.2(5H) 7.9~8.6(4H) |
| 3 | 22 | −N⌒N−CH₂CH(OC₂H₅)−C₆H₅ | −N(CH₂CH(CH₃)₂)(cyclohexyl) | 1.71 (59) | 580, 579, 535 445, 389 | 1600, 1560 1490, 1360 1160 | 0.5~2.3(20H) 2.4~3.7(15H) 4.3(1H), 7.2(5H) 7.8~8.8(4H) |
| 4 | 23 | −N⌒N−CH₂CH(OC₂H₅)−C₆H₅ | −N(CH₃)(C₆H₅) | 3.61 (68) | 533, 531, 487 473, 397 | 1600, 1550 1470, 1380 1170 | 1.0(3H), 2.0~2.7(10H) 3.15(2H), 3.5(3H) 4.2~4.5(1H), 7.3(10H) 7.5~8.8(4H) |
| 5 | 25 | −N⌒N−CH₂CH(OC₂H₅)−C₆H₅ | −N(CH₃)(CH₂−C₆H₅) | 4.2 (77) | 545, 500, 487 410 | 1600, 1560 1470, 1370 | 1.1(3H), 2.1~3.0(10H) 3.0~3.4(2H), 3.4(3H) 4.4(1H), 5.1(2H), 7.3(5H) 7.4(5H), 7.9~8.7(4H) |
| 6 | 26 | −N⌒N−CH₂CH(OCH₃)−C₆H₅ | −N(CH₃)(cyclohexyl) | 1.33 (84) | 523, 492, 402 | 1600, 1560 1470, 1360 1170 | 0.7~2.1(10H), 2.3~ 3.7(11H) 2.5(3H), 3.4(3H), 4.2(1H) 7.2(5H), 7.8~8.8(4H) |
| 7 | 27 | −N⌒N−CH₂CH(OCH(CH₃)₂)−C₆H₅ | −N(CH₃)(cyclohexyl) | 1.31 (79) | 552, 551, 492 402 | 1600, 1550 1470, 1370 1160 | 0.8~2.1(16H), 2.3~ 2.7(12H) 2.4(3H), 4.3(1H), 7.2(5H) 7.8~8.8(4H) |
| 8 | 28 | −N⌒N−CH₂CH(OCH₂CH(CH₃)₂)−C₆H₅ | −N(CH₃)(cyclohexyl) | 1.23 (76) | 566, 565, 492 402 | 1600, 1550 1470, 1360 1160 | 0.8~2.2(18H), 2.3~ 3.8(12H) 2.6(3H), 4.3(1H) 7.2(5H), 7.8~8.8(4H) |

TABLE 5-2-continued

6-Quinazolinesulfonyl Derivative of Formula (I)

| Run No. | Compound No. | $R_3$ | $-N\begin{smallmatrix}R_1\\R_2\end{smallmatrix}$ | Yield [g (%)] | Mass Spectrum | IR Absorption Spectrum ($\nu_{max}^{cap}$, cm$^{-1}$) | NMR Spectrum (CDCl$_3$) |
|---|---|---|---|---|---|---|---|
| 9 | 15 | $-N\underset{}{\underset{}{\bigcirc}}N-CH_2CH(OC_2H_5)-\bigcirc$ | $-NH-\bigcirc$ | 2.28 (87) | 524, 523, 479 464, 388 | 1590, 1560 1470, 1370 1170 | 0.8~3.7(27H), 4.4(1H) 7.2(5H), 7.9~8.7(4H) |
| 10 | 16 | $-N\underset{}{\underset{}{\bigcirc}}N-CH_2CH(OC_2H_5)-\bigcirc$ | $-NH-\bigcirc$ | 2.0 (77) | 517, 473, 383 | 1600, 1550 1470, 1370 1170 | 1.0(3H), 2.0~2.7(11H) 3.20(2H), 4.4(1H) 7.3(10H), 7.5~8.8(4H) |
| 11 | 17 | $-N\underset{}{\underset{}{\bigcirc}}N-CH_2CH(OC_2H_5)-\bigcirc$ | $-NHCH_2-\bigcirc$ | 0.88 (66) | 532, 531, 397 | 1600, 1550 1470, 1360 1160 | 1.1(3H), 2.1~3.0(11H) 3.0~3.4(2H), 4.4(1H) 5.1(2H), 7.3(5H), 7.4(5H) 7.9~8.7(4H) |

EXAMPLE 6

In 100 ml of a chloroform solution containing 4.96 g of 1-(2-isopropoxy-2-phenylethyl)piperazine was added 2.76 g of anhydrous potassium carbonate, and to the solution was added dropwise 50 ml of a chloroform solution containing 6.23 g of 4-piperidino-6-quinazolinesulfonyl chloride under cooling with ice. The solution thus obtained was stirred at a temperature of 20° C. to 25° C. and then the reaction solution was washed with water, dried with Glauber's salt, and then chloroform was distilled therefrom. The residue thus obtained was subjected to the same silica gel-column chromatography as in Example 1 using chloroform as the solvent to give 5.55 g of 1-(4-piperidino-6-quinazolinesulfonyl)-4-(2-isopropoxy-2-phenylethyl)piperazine [i.e., Compound (7)] in a yield of 53%.

Mass spectrum (m/e): 523, 465, 451, 374 and 307.

NMR spectrum (CDCl$_3$): 1.0~1.3(6H), 1.8(6H), 2.3~3.3(10H), 3.3~3.6(1H), 3.8(4), 4.4(1H), 7.2(5H) and 7.9~8.6(4H).

IR absorption spectrum ($\nu_{max}^{KBr}$, cm$^{-1}$), 2HCl salt: 1610, 1560, 1370 and 1310.

The same procedures as described above were repeated except that 5.50 g of 1-(2-isobutoxy-2-phenylethyl)piperazine was employed instead of the 4.96 g of 1-(2-isopropoxy-2-phenylethyl)piperazine, and there was prepared 1-(4-piperidino-6-quinazolinesulfonyl)-4-(2-isobutoxy-2-phenylethyl)piperazine [i.e., Compound (8)] in a yield of 49%.

Mass spectrum (m/e): 538, 465, 374 and 307.

NMR spectrum (CDCl$_3$): 0.82(6H), 1.5~2.2(7H), 2.3~3.3(12H), 3.8(4H), 4.2(1H), 7.2(5H) and 7.8~8.5(4H).

IR absorption spectrum ($\nu_{max}^{KBr}$, cm$^{-1}$), 2HCl salt: 1610, 1560, 1370 and 1310.

EXAMPLE 7

In 100 ml of a chloroform solution containing 4.04 g of 1-cinnamylpiperazine was added 2.76 g of anhydrous potassium carbonate and to the solution was added dropwise 50 ml of a chloroform solution containing 6.23 g of 4-piperidino-6-quinazolinesulfonyl chloride under cooling with ice. The solution thus obtained was stirred at a temperature of 20° C. to 25° C. for 5 hours and then the reaction solution was washed with water, dried with Glauber's salt, and then chloroform was distilled therefrom. The residue thus obtained was subjected to the same silica gel-column chromatography as in Example 1 using chloroform as the solvent to give 5.25 g of 1-(4-piperidino-6-quinazolinesulfonyl)-4-cinnamylpiperazine [i.e., Compound (9)] in a yield of 55%.

Mass spectrum (m/e): 478, 387, 357 and 305.

NMR spectrum (CDCl$_3$): 1.6(6H), 2.3~3.2(10H), 3.6~3.8(4H), 5.8~6.5(2H), 7.2(5H) and 7.9~8.6(4H).

1-(4-Piperidino-6-quinazolinesulfonyl)-4-cinnamylpiperazine.2HCl

Melting point: 242°~247° C. (decomp.)

IR absorption spectrum ($\nu_{max}^{KBr}$, cm$^{-1}$): 3420, 1605, 1560, 1360 and 1160.

Relaxation of Mesenteric Artery

After a home bred rabbit of a Japanese species weighing about 3 Kg was subjected to bloodletting, resulting in death and then to abdominal incision, the mesenteric artery was taken out, cut into helicoids of 2 mm×25 mm and suspended in a 20 ml organ bath filled with a Krebs-Henseleit solution into which a mixed gas of 95% by volume of $O_2$ and 5% by volume of $CO_2$ was introduced and one end of the artery was connected with an isometric transducer. When a load of 1.5 g was applied to the artery, the contraction and the relaxation of the artery was recorded as a weight on the transducer (a product of Nippon Koden K.K., Japan, "FD Pickup TB-912T"). The relaxation of the mesenteric artery was observed by adding the 6-quinazolinesulfonyl derivatives and their pharmaceutically acceptable acid addition salts to the mesenteric artery at the condition of about one half of the maxinum contraction with KCl at a KCl concentrantion of 15~20 mM. When the complete relaxation of the mesenteric artery was designated 100%, the concentration of the 6-quinazolinesulfonyl derivatives and their pharmaceutically acceptable acid addition salts which brought about a relaxation of 50% is shown in Table 6.

TABLE 6

| Compound Nos. | Relaxation of Mesenteric Artery ED$_{50}$ (μM) |
|---|---|
| (1) | 9.8 |
| (2) | 4.5 |

TABLE 6-continued

| Compound Nos. | Relaxation of Mesenteric Artery ED$_{50}$ ($\mu$M) |
|---|---|
| (3) | 5.0 |
| (4) | 1.3 |
| (5) | 5.8 |
| (6) | 1.7 |
| (7) | 2.2 |
| (8) | 10.7 |
| (9) | 3.0 |
| (14) | 9.5 |
| (15) | 1.6 |
| (16) | 2.7 |
| (17) | 3.2 |
| (18) | 1.4 |
| (19) | 0.8 |
| (20) | 3.7 |
| (22) | 2.5 |
| (23) | 2.2 |
| (25) | 0.8 |
| (26) | 1.4 |
| (27) | 0.9 |
| (28) | 1.3 |
| (29) | 33 |
| (30) | 30 |
| (31) | 21 |
| (32) | 24 |
| (33) | 34 |
| (34) | 27 |
| (35) | 54 |
| (36) | 50 |
| (37) | 8.0 |
| (38) | 12 |

Effect on c-AMP-decomposing PDE and Calmodulin or Calcium-dependent Cyclic Nucleotide PDE As the enzyme specimens, human blood platelet and hog cerebral cortex were partially purified in accordance with reports [Mol. Pharmacol., 15, 49 (1979) and Biochem. Biophys. Res. Comun., 84, 277 (1978)]. The effect of the 6-quinazolinesulfonyl derivatives and their pharmaceutically acceptable acid addition salts of this invention on the c-AMP-decomposing PDE and the calmodulin or calcium-dependent cyclic nucleotide PDE was examined under the conditions in accordance with the above described reports. The results are shown in Table 7. The compounds of this invention inhibited the decomposition due to the enzyme specimens of the substrate c-AMP and c-GMP. The activity of the compounds of this invention is expressed by the concentration which is required to inhibit 50% of the decomposition of the c-AMP-decomposing PDE, i.e., I$_{50}$ by $\mu$M.

TABLE 7

| | PDE Inhibition I$_{50}$ | | |
|---|---|---|---|
| | Human Blood | Hog Cerebral Cortex (P$_{II}$)*2 | |
| Compound Nos. | Platelet (P$_{II}$)*1 ($\mu$M) | Non-activated ($\mu$M) | Activated ($\mu$M) |
| (4) | 950 | not inhibited | 370 |
| (6) | 850 | 15 | 31 |
| (9) | 700 | not inhibited | 20 |
| (19) | 750 | 4 | 4 |
| (23) | 900 | 24 | 11 |
| (25) | 850 | 7 | 7 |
| (31) | 300 | 88 | 75 |
| (32) | 520 | 94 | 111 |
| (37) | 250 | 109 | 44 |

Note:
*1 The human blood platelet c-AMP PDE specimen was employed.
*2 The enzyme activity was measured by using calmodulin and Ca$^{++}$ dependent specimens. The non-activation was measured in the presence of 0.2 mM of EGTA, while the activation was measured in the presence of 0.2 mM of CaCl$_2$ and 8 units of calmodulin.

Effect on Blood Flow Volume of Femoral and Vertebral Arteries of Dog

The effect on the vasodilatation of the femoral and vertebral arteries was measured by anesthetizing a dog of mixed breed weighing 8 to 15 Kg by an intravenous administration of 35 mg/Kg of pentbarbital, providing an acute type probe (a product of Nippon Koden K.K., Japan) with the femoral and vertebral arteries, administering the 6-quinazolinesulfonyl derivatives and their pharmaceutically acceptable acid addition salts to the femoral vein through a polyethylene tube inserted into the femoral vein side chain and measuring the blood flow volume with an electromagnetic blood flowmeter (a product of Nippon Koden K.K., Japan, "MF-27"). The results are shown in Table 8.

TABLE 8

| Compound Nos. | Amount of Intravenous Administration (mg/Kg) | Increased Blood Flow Volume in Femoral Artery (%) | Increased Blood Flow Volume in Vertebral Artery (%) |
|---|---|---|---|
| (4) | 1 | 33 | 50 |
| (6) | 1 | 31 | 51 |
| (9) | 1 | 24 | 42 |
| (19) | 1 | 33 | 59 |
| (23) | 1 | 25 | 38 |
| (25) | 1 | 36 | 48 |
| (31) | 1 | 28 | 48 |
| (32) | 1 | 21 | 36 |
| (37) | 1 | 24 | 41 |

Acute Toxicity

The acute toxicity of the 6-quinazolinesulfonyl derivatives and their pharmaceutically acceptable acid addition salts was measured by giving male ddY-strain mice an intravenous administration. The results are shown in Table 9.

TABLE 9

| Compound Nos. | LD$_{50}$ (mg/Kg) |
|---|---|
| (4) | 135 |
| (6) | 108 |
| (9) | 133 |
| (19) | 63 |
| (23) | 98 |
| (25) | 72 |
| (31) | 45 |
| (32) | 95 |
| (37) | 103 |

While the invention has been described in detail and with reference to specific embodiments thereof, it will be apparent to one skilled in the art that various changes and modifications can be made therein without departing from the spirit and scope thereof.

What is claimed is:

1. A compound of Formula (I):

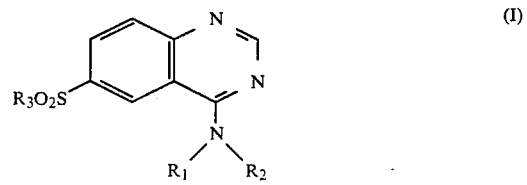

(I)

wherein
R$_1$ is a hydrogen atom or a C$_{1-12}$ alkyl group;

$R_2$ is a hydrogen atom, a $C_{1-12}$ alkyl group, a $C_{4-10}$ cycloalkyl group, an aryl group or an aralkyl group; and $R_1$ and $R_2$ may be linked directly or through an oxygen atom to form a 5- to 7-membered heterocyclic ring together with the adjacent nitrogen atom; and $R_3$ is a

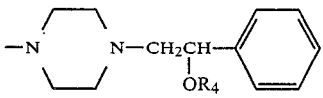

group wherein $R_4$ is a $C_{1-8}$ alkyl group; a —$NH(CH_2)_nNH_2$ group wherein n is an integer of 2 to 10; or a

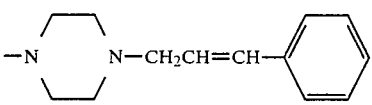

group;

and the pharmaceutically acceptable acid addition salt thereof.

2. A compound of claim 1 of Formula (I):

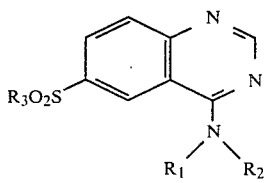

(I)

wherein $R_1$ is a hydrogen atom or a $C_{1-6}$ alkyl group;

$R_2$ is a hydrogen atom, a $C_{1-6}$ alkyl group, a $C_{5-7}$ cycloalkyl group, a phenyl group, benzyl group or a phenethyl group; and $R_1$ and $R_2$ may be linked directly or through an oxygen atom to form a 5- or 6-membered heterocyclic ring together with the adjacent nitrogen atom; and $R_3$ is a

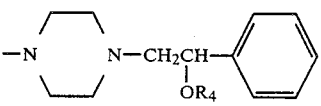

group wherein $R_4$ is a $C_{1-4}$ alkyl group; a —$NH(CH_2)_nNH_2$ group wherein n is an integer of 2 to 10; or a

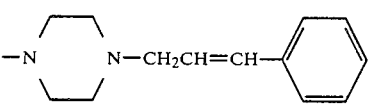

group;

and the pharmaceutically acceptable acid addition salt thereof.

3. The compound of claim 2, wherein the

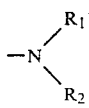

group is a 1-pyrrolidinyl group, a piperidino group, a homopiperidino group or a morpholino group and $R_3$ is a —$HN(CH_2)_nNH_2$ group wherein n is an integer of 2 to 10.

4. The compound of claim 3, wherein the

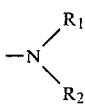

group is a piperidino group and $R_3$ is a —$HN(CH_2)_nNH_2$ group wherein n is an integer of 2 to 10.

5. The compound of claim 4, wherein the

group is a piperidino group and $R_3$ is a —$HN(CH_2)_4NH_2$ group.

6. The compound of claim 4, wherein the

group is a piperidino group and $R_3$ is a —$HN(CH_2)_6NH_2$ group.

7. The compound of claim 2, wherein $R_1$ and $R_2$ are $C_{1-6}$ alkyl groups and $R_3$ is a —$HN(CH_2)_nNH_2$ group wherein n is an integer of 2 to 10.

8. The compound of claim 7, wherein $R_1$ and $R_2$ are n-butyl groups and $R_3$ is a —$HN(CH_2)_4NH_2$ group.

9. The compound of claim 2, wherein the

group is a 1-pyrrolidinyl group, a piperidino group, a homopiperidino group or a morpholino group and $R_3$ is a

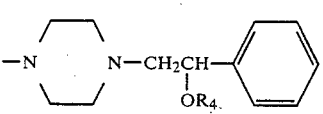

group wherein $R_4$ is a $C_{1-4}$ alkyl group.

10. The compound of claim 9, wherein the

group is a piperidino group and $R_3$ is a

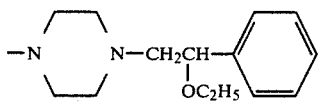

group.

11. The compound of claim 2, wherein $R_1$ and $R_2$ are $C_{1-6}$ alkyl groups and $R_3$ is a

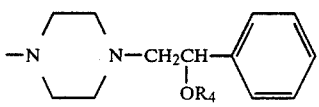

group wherein $R_4$ is a $C_{1-4}$ alkyl group.

12. The compound of claim 11, wherein $R_1$ and $R_1$ are n-butyl groups and $R_3$ is a

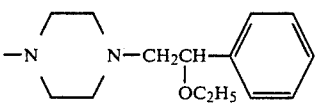

group.

13. The compound of claim 2, wherein $R_1$ is a $C_{1-6}$ alkyl group, $R_2$ is a $C_{5-7}$ cycloalkyl group and $R_3$ is a

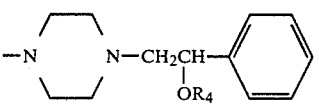

group wherein $R_4$ is a $C_{1-4}$ alkyl group.

14. The compound of claim 13, wherein $R_1$ is a methyl group, $R_2$ is a cyclohexyl group and $R_3$ is a

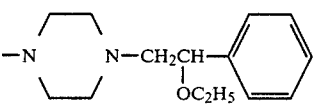

group.

15. The compound of claim 2, wherein $R_1$ is a $C_{1-6}$ alkyl group, $R_2$ is an aryl group and $R_3$ is a

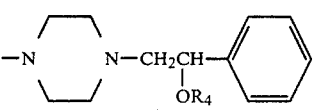

group wherein $R_4$ is a $C_{1-4}$ alkyl group.

16. The compound of claim 15, wherein $R_1$ is a methyl group, $R_2$ is a phenyl group and $R_3$ is a

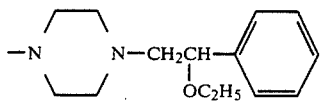

group.

17. The compound of claim 2, wherein $R_1$ is a $C_{1-6}$ alkyl group, $R_2$ is an aralkyl group and $R_3$ is a

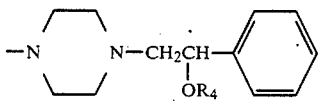

group wherein $R_4$ is a $C_{1-4}$ alkyl group.

18. The compound of claim 17, wherein $R_1$ is a methyl group, $R_2$ is a benzyl group and $R_3$ is a

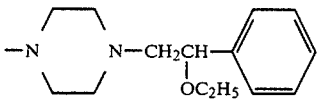

group.

19. The compound of claim 2, wherein $R_1$ and $R_2$ are hydrogen atoms and $R_3$ is a

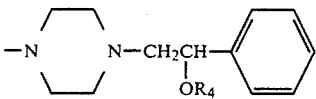

group wherein $R_4$ is a $C_{1-4}$ alkyl group.

20. The compound of claim 2, wherein $R_1$ a hydrogen atom, $R_2$ is a $C_{5-7}$ cycloalkyl group and $R_3$ is a

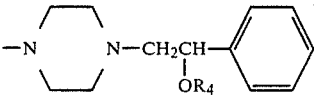

group wherein $R_4$ is a $C_{1-4}$ alkyl group.

21. The compound of claim 2, wherein $R_1$ is a hydrogen atom, $R_2$ is a phenyl group and $R_3$ is a

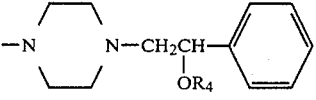

group wherein $R_4$ is a $C_{1-4}$ alkyl group.

22. The compound of claim 2, wherein $R_1$ is a hydrogen atom, $R_2$ is a benzyl group and $R_3$ is a

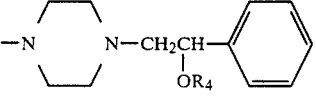

group wherein $R_4$ is a $C_{1-4}$ alkyl group.

23. The compound of claim 2, wherein the

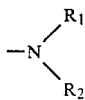

group is a 1-pyrrolidinyl group, a piperidino group, a homopiperidino group or a morpholino group and $R_3$ is a

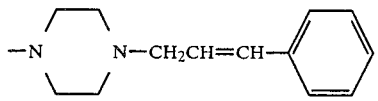

group.

24. The compound of claim 23, wherein the

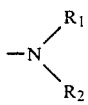

is a piperidino group and $R_3$ is a

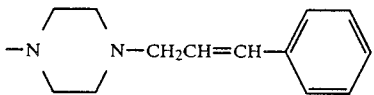

group.

25. A process of preparing the compound of claim 1 which comprises reacting a compound of Formula (II):

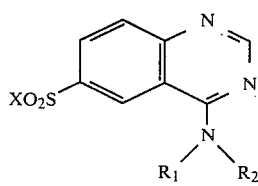

wherein
$R_1$ is a hydrogen atom or a $C_{1-12}$ alkyl group;
$R_2$ is a hydrogen atom, a $C_{1-12}$ alkyl group, a $C_{4-10}$ cycloalkyl group, an aryl group or an aralkyl group; and
$R_1$ and $R_2$ may be linked directly or through an oxygen atom to form a 5- to 7-membered heterocyclic ring together with the adjacent nitrogen atom; and
X is a chlorine atom or a bromine atom,
with a compound of Formula (III):

$R_3H$      (III)

wherein
$R_3$ is a

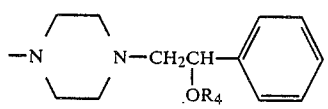

group wherein $R_4$ is a $C_{1-8}$ alkyl group; a $-NH(CH_2)_nNH_2$ group wherein n is an integer of 2 to 10; or a

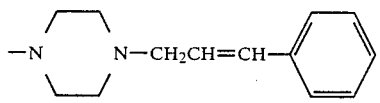

group.

26. The process of claim 25, wherein the amount of the compound of Formula (III) is about 1 to about 10 mols per mol of the compound of Formula (II).

27. The process of claim 26, wherein the amount of the compound of Formula (III) is 1.0 to 5 mols per mol of the compound of Formula (II).

28. The process of claim 25, wherein the reaction between the compound of Formula (II) and the compound of Formula (III) is carried out in the presence of an acid acceptor.

29. The process of claim 28, wherein the acid acceptor is an alkali metal compound or an organic tertiary amine.

30. The process of claim 29, wherein the alkali metal compound is a hydroxide, a bicarbonate, a carbonate, a hydride or an alkoxide of an alkali metal.

31. The process of claim 28, wherein the amount of the acid acceptor is about 1 to about 10 equivalents for each mol of the compound of Formula (III).

32. The process of claim 31, wherein the amount of the acid acceptor is 1 to 6 equivalents for each mol of the compound of Formula (III).

33. The process of claim 25, wherein the reaction between the compound of Formula (IV) and the amine of Formula (V) is carried out in the presence of a reaction medium.

34. The process of claim 33, wherein the reaction medium is a halogenated hydrocarbon, an alkanol, an ether, N,N-dimethylformamide, dimethyl sulfoxide, acetonitrile, water or a mixture thereof.

35. The process of claim 25, wherein the reaction temperature is about $-30°$ C. to about $150°$ C.

36. The process of claim 35, wherein the reaction temperature is about $0°$ C. to about $30°$ C.

37. A process of preparing the compound of claim 1 which comprises reacting a compound of Formula (IV):

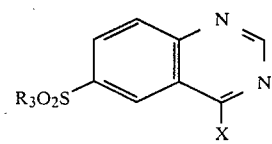

wherein
$R_3$ is a

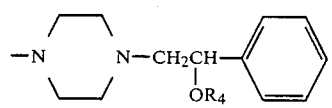

group wherein $R_4$ is a $C_{1-8}$ alkyl group; a $-NH(CH_2)_nNH_2$ group wherein n is an integer of 2 to 10; or a

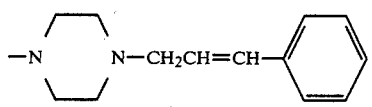

group; and

X is a chlorine atom or a bromine atom, with an amine of Formula (V):

wherein

R₁ is a hydrogen atom or a $C_{1-12}$ alkyl group;

R₂ is a hydrogen atom, a $C_{1-12}$ alkyl group, a $C_{4-10}$ cycloalkyl group, an aryl group or an aralkyl group; and R₁ and R₂ may be linked directly or through an oxygen atom to form a 5- to 7-membered heterocyclic ring together with the adjacent nitrogen atom, or the acid addition salt thereof.

38. The process of claim 37, wherein the amount of the amine of Formula (V) is about 1 to about 20 mols per mol of the compound of Formula (IV).

39. The process of claim 38, wherein the amount of the amine of Formula (V) is 1.2 to 10 mols per mol of the compound of Formula (IV).

40. The process of claim 37, wherein the reaction between the compound of Formula (IV) and the amine of Formula (V) is carried out in the presence of an acid acceptor.

41. The process of claim 40, wherein the acid acceptor is an alkali metal compound or an organic tertiary amine.

42. The process of claim 41, wherein the alkali metal compound is a hydroxide, a bicarbonate, a carbonate, a hydride or an alkoxide of an alkali metal.

43. The process of claim 40, wherein the amount of the acid acceptor is about 1 to about 10 equivalents for each mol of the amine of Formula (V).

44. The process of claim 43, wherein the amount of the acid acceptor is 1 to 4 equivalents for each mol of the amine of Formula (V).

45. The process of claim 37, wherein the reaction between the compound of Formula (IV) and the amine of Formula (V) is carried out in the presence of a reaction medium.

46. The process of claim 45, wherein the reaction medium is a halogenated hydrocarbon, an alkanol, an ether, N,N-dimethylformamide, dimethyl sulfoxide, acetonitrile, water or a mixture thereof.

47. The process of claim 37, wherein the reaction temperature is about −30° C. to about 150° C.

48. The process of claim 47, wherein the reaction temperature is about 0° C. to about 60° C.

49. A compound of Formula (II):

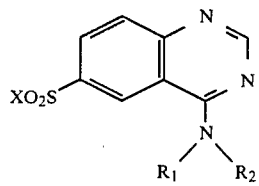

wherein

R₁ is a hydrogen atom or a $C_{1-12}$ alkyl group;

R₂ is a hydrogen atom, a $C_{1-12}$ alkyl group, a $C_{4-10}$ cycloalkyl group, an aryl group or an aralkyl group; and R₁ and R₂ may be linked directly or through an oxygen atom to form a 5- to 7-membered heterocyclic ring together with the adjacent nitrogen atom; and X is a halogen atom.

50. The compound of claim 49, wherein the

group is a 1-pyrrolidinyl group, a piperidino group, a homopiperidino group or a morpholino group and X is a chlorine atom or a bromine atom.

51. The compound of claim 50, wherein the

group is a piperidino group and X is a chlorine atom.

52. The compound of claim 49, wherein the

group is a 1-pyrrolidinyl group and X is a chlorine atom.

53. The compound of claim 49, wherein R₁ and R₂ are $C_{1-6}$ alkyl groups and X is a chlorine atom.

54. A compound of Formula (IV):

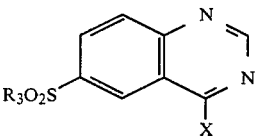

wherein

X is a halogen atom; and

R₃ is a

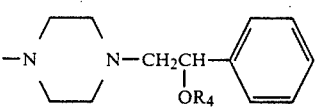

group wherein $R_4$ is a $C_{1-8}$ alkyl group; a —$NH(CH_2)_nNH_2$ group wherein n is an integer of 2 to 10; or a

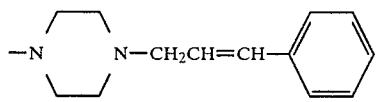

group.

55. The compound of claim 54, wherein X is a chlorine atom or a bromine atom and $R_3$ is a

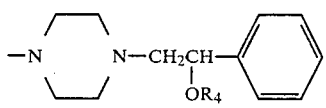

group wherein $R_4$ is a $C_{1-4}$ alkyl group.

56. The compound of claim 54, wherein X is a chlorine atom or a bromine atom and $R_3$ is a

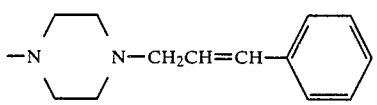

group.

57. The compound of claim 54, wherein X is a chlorine atom or a bromine atom and $R_3$ is a —$HN(CH_2)_nNH_2$ group wherein n is an integer of 2 to 10.

58. A compound of Formula (VI):

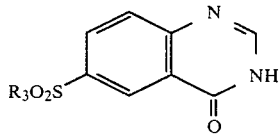

(VI)

wherein
$R_3$ is a

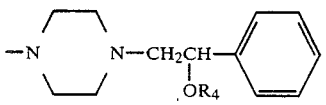

group wherein $R_4$ is a $C_{1-8}$ alkyl group; a —$HN(CH_2)_nNH_2$ wherein n is an integer of 2 to 10; or a

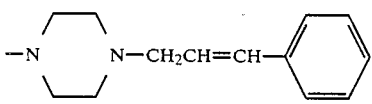

group.

59. The compound of claim 58, wherein $R_3$ is a

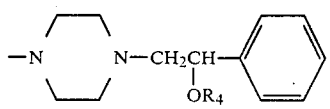

group wherein $R_4$ is a $C_{1-4}$ alkyl group.

60. A process of preparing the compound of claim 58 which comprises reacting 3,4-dihydro-4-oxo-6-quinazolinesulfonyl chloride or bromide with a compound of Formula (III):

$R_3H$             (III)

wherein
$R_3$ is a

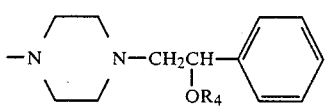

group wherein $R_4$ is a $C_{1-8}$ alkyl group; a —$HN(CH_2)_nNH_2$ wherein n is an integer of 2 to 10 or a

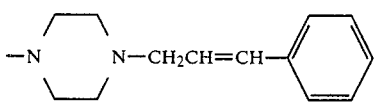

group.

61. The process of claim 60, wherein $R_3$ in Formula (III) is a

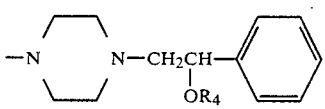

group wherein $R_4$ is a $C_{1-4}$ alkyl group.

62. The process of claim 60, wherein the reaction is carried out in the presence of a reaction medium.

63. The process of claim 62, wherein the reaction medium is chloroform.

64. The process of claim 60, wherein the reaction is carried out in the presence of about 1 to about 5 mols of anhydrous potassium carbonate per mol of the 3,4-dihydro-4-oxo-quinazolinesulfonyl chloride or bromide.

65. The process of claim 60, wherein the reaction temperature ranges about 10° C. to about 30° C.

66. A process of preparing the compound of claim 54 which comprises reacting a compound of Formula (VI) of claim 58 with a halogenating agent.

67. The process of claim 66, wherein the amount of the halogenating agent ranges from about 3 to about 30 mols per mol of the compound of Formula (VI).

68. The process of claim 66, wherein the reaction is carried out in the presence of an inert reaction medium.

69. The process of claim 66, wherein the reaction temperature ranges from about 20° C. to about 200° C.

70. The process of claim 69, wherein the reaction temperature ranges from about 60° C. to about 150° C.

71. The process of claim 70, wherein the reaction temperature ranges from about 70° C. to about 120° C.

72. The process of claim 66, wherein the halogenating agent is thionyl chloride, phosphorus oxychloride, phosphorus trichloride, phosphorus tribromide and phosphorus pentachloride.

73. The process of claim 72, wherein the halogenating agent is thionyl chloride.

74. The process of claim 68, wherein the inert reaction medium is N,N-dimethylformamide.

* * * * *